United States Patent [19]
Gross

[11] Patent Number: 5,479,019
[45] Date of Patent: Dec. 26, 1995

[54] APPARATUS FOR DETERMINING THE $^{13}CO_2/^{12}CO_2$ RATIO OF CONCENTRATIONS IN A GAS SAMPLE

[75] Inventor: Joachim Gross, Solothurn, Switzerland

[73] Assignee: MIC Medical Instrument Corporation, Solothurn, Switzerland

[21] Appl. No.: 266,628

[22] Filed: Jun. 28, 1994

[30] Foreign Application Priority Data

Jul. 13, 1993 [CH] Switzerland ............................ 2095/93

[51] Int. Cl.[6] ................................................... G01N 21/61
[52] U.S. Cl. .............................................................. 250/345
[58] Field of Search ...................................... 250/345, 343

[56] References Cited

U.S. PATENT DOCUMENTS

| | | | |
|---|---|---|---|
| 4,684,805 | 8/1987 | Lee et al. ................................. | 250/345 |
| 5,146,294 | 9/1992 | Grisar et al. ............................ | 250/345 |
| 5,317,156 | 5/1994 | Cooper et al. .......................... | 250/345 |

FOREIGN PATENT DOCUMENTS

| | | |
|---|---|---|
| 1240307 | 5/1967 | Germany . |
| 734578 | 8/1955 | United Kingdom . |
| 2218514 | 11/1989 | United Kingdom . |

*Primary Examiner*—Carolyn E. Fields
*Attorney, Agent, or Firm*—Oblon, Spivak, McClelland, Maier & Neustadt

[57] ABSTRACT

A measuring apparatus based on the NDIR process. Pulsed infrared light traverses in two parallel optical beams (3, 4) initially a cell (6) filled with $^{13}CO_2$ and a cell (7) filled with $^{12}CO_2$ and then, in parallel, two cells (8, 9) which are filled with the gas sample to be analyzed. Cells (8, 9) together with a capacitor microphone (15) serving as the pressure converting means form an optopneumatic receiver (17). By regulating the pressure in cell (6) the minimum of the pressure conversion signal is investigated and related to a correspondingly obtained reference value. The simply constructed apparatus permits a $^{13}CO_2$ breathing test to be performed inexpensively.

20 Claims, 3 Drawing Sheets

APPARATUS FOR DETERMINING THE $^{13}CO_2/^{12}CO_2$ RATIO OF CONCENTRATIONS IN A GAS SAMPLE

BACKGROUND OF THE INVENTION

1. Field of the Invention

The present invention relates to an apparatus based on the non-dispersive infrared (NDIR) process for the determination of the $^{13}CO_2/^{12}CO_2$ ratio of concentrations in a gas sample.

2. Discussion of the Background

Various substances which are metabolized by the body can be provided with a nonradioactive label, and detected by their metabolic reaction products. One of the essential products of the metabolism of carbon compounds is the $CO_2$ molecule. If a carbon-containing compound is labelled at a suitable point in the molecule by a $^{13}C$-atom and said compound is administered to a patient, the $^{13}CO_2$ formed therefrom in the patient's body can be detected in the respiratory air. An important use for this technique is in the diagnosis of an infection by *Heliobacter pylori*, which is the cause of gastric and duodenal ulcers. A $^{13}C$-labelled urea is administered to the patient and $^{13}CO_2$ is formed from it by urease of the bacterium (cf. also R. P. H. Logan et al, European Journal of Gastroenterology & Hepatology 1991, vol. 3, no. 12, pp. 915–921).

Other uses are:

lipase deficiency in pancreatic juices after administering $^{13}C$-labelled triglycerides or triolein;

hepatic cirrhosis or chronic hepatitis after administering $^{13}C$-aminopyrine, $^{13}C$-phanacetin or $^{13}C$-galactose;

absorbtion of harmful substances from the environment, such as PCB after administering $^{13}C$-caffeine.

For all these uses the $^{13}C$-breathing test is a highly appropriate, non-invasive diagnosis method. Due to the very high prices for $^{13}C$-labelled substances and for the necessary detection equipment, these tests have been used almost exclusively in research, and for infants, where the alternatively available biopsy sample tests could not be used. Serological tests offer another alternative but suffer from the disadvantage that they remain positive for a long time after the bacterium has been eradicated.

Investments in facilities for the production of $^{13}C$ have taken place at numerous locations and it is expected that $^{13}C$-product prices will drop in the future. However, in order for the respiratory or breathing tests to become attractive, it is also necessary to make available inexpensive detection equipment. The requirements on a measuring process for the detection of $^{13}CO_2$ or for the determination of the $^{13}CO_2/^{12}CO_2$ ratio of concentrations in the respiratory air of a patient are very demanding. For example, following the ingestion of a urea product by a patient infected with *Heliobacter pylori*, in the period between approximately 5 and 60 minutes after ingesting the product, the isotope ratio rises only from approximately 1.0% (i.e., the normal value corresponding to the natural isotope ratio) to approximately 1.03%. In general, mass spectrometers have been used up to now for detecting this extremely small concentration increase. The very high price of such equipment (approximately 100,000 U.S. dollars) has made it necessary to send the respiratory gas samples to special laboratories having such an apparatus and where the analysis is performed. The resulting logistic and financial costs have constituted a further massive obstacle to widespread use of the $^{13}CO_2$ respiratory gas test.

There is consequently a need for an inexpensive apparatus for $^{13}CO_2$ respiratory gas tests which an ordinary doctor or at least a small laboratory can afford and which permits simple, reliable operation by unspecialized personnel.

A first step in the direction of such an apparatus has recently been taken at the Düsseldorf Laser Medicine Institute by P. Hering and M. Haisch. In the apparatus produced there, which is based on the apparatus according to DE-AI-3522949, pulsed infrared light passes in parallel to, in each case, one cell through which flows a gas sample to be analyzed and is subsequently detected with two optopneumatic receivers. The optopneumatic receivers comprise in each case two gas-filled cells, which are linked to one another by means of a capacitor microphone and whereof one is traversed in each optical path by the infrared light. The capacitor microphones convert the pressure fluctuations produced by the absorbtion of the pulsating infrared light in the particular irradiated cell into electrical signals. For calibrating the apparatus to the normal $^{13}CO_2/^{12}CO_2$-ratio, special calibrating cells are provided, which are filled with a gaseous mixture having said ratio. They are introduced into the optical paths, but are removed again therefrom for the actual measurement. The amplitudes of the signals supplied by the optopneumatic receivers are compared with one another and the difference of said signals determines the measurement signal. However, quite apart from the fact that this determination requires complicated electronics, this process suffers from the disadvantages that measuring errors, and calibrating errors, and environmental influences enter into the desired measurement result in a highly sensitive manner.

SUMMARY OF THE INVENTION

An object of the present invention is to provide an apparatus for determining the $^{13}CO_2/^{12}CO_2$ ratio in the respiratory air of a patient, which has a simple construction, is inexpensive to manufacture, easy to operate and largely independent of environmental influences comprising: a pulsating infrared light source, two first cells traversed in parallel by the light from said light source one containing substantially only $^{13}CO_2$ and the other containing substantially only $^{12}CO_2$; two second cells also traversed in parallel by the light of the infrared light source and in each case containing one part of the gas sample; first pressure converting means having a diaphragm for converting periodic pressure fluctuations caused by the absorbtion of said light in two of said cells into electrical signals; wherein said two first cells are located in the optical path upstream of said two second cells, the pressure in one of said two first cells is adjustable and the diaphragm of said first pressure converting means is positioned in such a way that it is sensitive to pressure fluctuations in each of said two second cells.

DETAILED DESCRIPTION OF THE PREFERRED EMBODIMENTS

In the apparatus according to the invention the two second cells together with the pressure converting means form an optopneumatic receiver. The apparatus according to the invention only requires one such receiver, but its two cells are located in different optical paths. The cells of the optopneumatic receiver are supplied with a gas sample to be analyzed, particularly a respiratory air sample, whereas the first cells located upstream in the optical paths are constantly filled with $^{13}CO_2$-gas on the one hand and $^{12}CO_2$-gas on the other By varying the pressure in one of the two last-mentioned cells it is possible to determine for the gas sample to be analyzed, as well as for a reference sample, the amplitude minimum of the signal produced by the optopneumatic receiver. The measured quantity is then easily obtained from the pressure difference.

Consequently the apparatus makes use of a balancing process, where many possible measuring and calibrating errors and environmental influences compensate one another on the physical plane of the measuring apparatus and cannot enter the measurement result. The apparatus according to the invention is very simple and can be operated by unspecialized personnel.

Advantageous embodiments of the invention relate to the arrangement of the diaphragm in the pressure converting means and measures for increasing the sensitivity of the apparatus. The sensitivity can be significantly increased if the optopneumatic receiver is constructed as a resonant system matched to the frequency of the pulsating infrared light source. For this purpose it is sufficient if the two cells communicate with one another by means of a connecting line of suitable length. The supply of the particular gas to be analyzed to the two cells of the optopneumatic receiver can take place very simply without disturbing the resonant system by means of two capillaries, if an opening to the environment is provided in the connecting line between the two cells, namely where there is a node of longitudinal wave in the case of resonance. Determination of the reference value can be facilitated in that a further optopneumatic receiver, identical to that already described, is located in the two optical paths. The cells of the further receiver can either be permanently filled with a $^{13}CO_2/^{12}CO_2$-gaseous mixture of known composition or in the same way as described hereinbefore with a reference gas described hereinbefore with a reference gas sample, e.g. a respiratory gas reference sample of the patient. The cells of the further optopneumatic receiver can advantageously remain in the optical paths during the measurement of the gas sample, so that they can be installed there in a fixed manner and there is no need for a complicated mechanism for their introduction or removal with respect to the optical paths. This also avoids the errors which could arise due to positioning inaccuracies in the case of movable reference cells.

Figure 1:
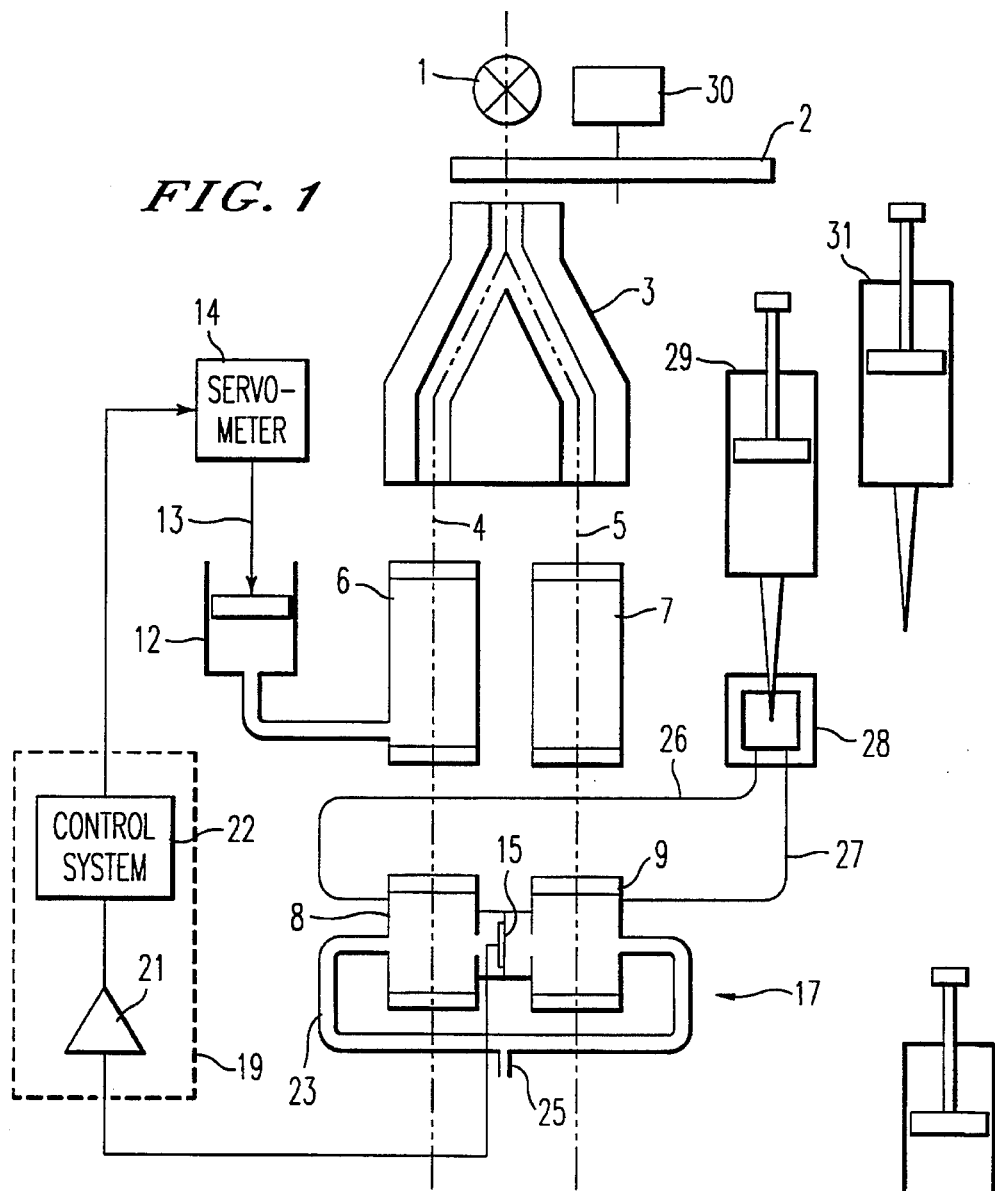
FIG. 1 shows a first embodiment of an apparatus according to the invention with only one optopneumatic receiver.

Referring to FIG. 1, infrared light source 1 is preferably a low voltage tungsten halogen lamp. The light of light source 1 is periodically interrupted by means of a motor-driven impeller 2 and is subsequently split in a beam splitter 3 into two partial beams 4 and 5 preferably having the same intensity. The beam splitter can be constituted by a metal block provided with a Y-hole and in whose holes is guided the light by multiple reflection as in light guides. The two partial beams 4, 5 then pass through two first cells 6, 7 and subsequently two second cells 8, 9. The cells are in each case provided with entrance and exit windows, which transmit at least the infrared fraction of the light of light source 1.

Cell 6 is filled with $^{12}CO_2$-gas and cell 7 with $^{13}CO_2$-gas. The pressure of the $^{12}CO_2$-gas in cell 6 is adjustable by means of a pressure cylinder 12 and a servomotor 14 acting thereon by means of a micrometer screw 13.

The two second cells 8, 9 are interconnected by means of the diaphragm of a capacitor microphone 15 (pressure converting means) and form, together with said capacitor microphone, an optopneumatic receiver 17. The diaphragm of the capacitor microphone 15 forms a common wall part of the two second cells 8, 9.

The leads of the capacitor microphone 15 are connected to an electronic unit 19 and connected to the input of an amplifier 21. A control system 22 supplied with the output signal of the amplifier 20 acts on the servomotor 14 in such a way that the amplifier output signal is at a minimum level.

The two second cells 8, 9 are in communicating connection by means of a line 23, which has in its centre an opening 25 to the environment. To the two second cells 8, 9 are also connected lines 26, 27, which at the other end emanate from a distributor block 28, to which can be connected a container filled with a gas sample to be analyzed; here in the form of syringes 29 or 31. By means of said syringes 29, 31 the two second cells 8, 9 can be supplied by means of lines 26, 27 with the particular gas to be analyzed, the gas previously in them escaping to the environment by means of the opening 25 in the connecting line 23 and consequently ambient pressure is obtained in the second cells 8, 9 automatically.

The function of the described apparatus is based on the different absorbtion characteristics of $^{12}CO_2$ and $^{13}CO_2$ in the infrared range. Therefore, following the cells 6 and 7 and in both optical beams 4 and 5, the light of the light source 1 has a somewhat different spectral composition. In the optical path 4 behind the cell 6 frequencies absorbed by $^{12}CO_2$ are attenuated and in the optical path 5 behind the cell 7 the frequencies absorbed by $^{13}CO_2$ are attenuated. Thus, in the cells 8, 9 of the optopneumatic receiver 17 there is generally a different absorbtion, which leads to different-pressure fluctuations with the rhythm of the pulsating light. By a suitable modification of the pressure in the cell 6, the difference of the pressure amplitudes in the cells 8, 9 can be minimized, and, in the case of complete synchronism of the light pulses in the two optical paths 4 and 5, can be made to disappear. This function is fulfilled by the aforementioned control system 22.

In order to increase the sensitivity during said balancing, the length of connecting line 23 is chosen in such a way that, with respect to the periodic pressure fluctuations in the second cells 8, 9 and the connecting line 23, there is a standing wave with an antinode of the longitudinal wave on the diaphragm of the capacitor microphone 15. In practice, after choosing the length of the connecting line 23, the frequency of the pulsating light will be adjusted by regulating the speed of the motor 30 driving the impeller 2 to the desired resonance condition.

In order that the two lines 26, 27 for supplying the second cells 8, 9 do not disturb the resonant system, they are at least zonely constructed as capillaries. Moreover, the opening 25 in the connecting line 23 does not have a disadvantageous influence on the formation of a standing wave if the opening 25 is located precisely where said standing wave forms a node of the longitudinal wave. With a symmetrical construction of the optopneumatic receiver 17, this is in the centre of the connecting line 23.

For performing a measurement the cells 8, 9 of the optopneumatic receiver 17 are firstly scavenged with a reference gas sample, e.g. from syringe 29 and subsequently the above-described balancing is carried out. As a result a reference value corresponding to a first position of the micrometer screw 13 is obtained. The two second cells 8, 9 of the optopneumatic receiver 17 are then supplied with the gas sample to be tested, e.g. by the syringe 31 and the same balancing is again carried out. This leads to a second position of the micrometer screw. After prior calibration of the apparatus with different samples of known composition, from the difference between the two micrometer screw positions it is possible to directly draw conclusions concerning the $^{13}CO_2/^{12}CO_2$-ratio of concentrations to be determined in the gas sample tested in the second stage.

The reference gas sample can be constituted by a reference gas of known composition or a respiratory gas sample of the patient immediately prior to the ingestion of the $^{13}CO_2$-product. The latter has the advantage that the measurement is independent of the natural $^{13}CO_2/^{12}CO_2$-ratio of concentrations in the expiratory air, which varies somewhat as a function of the nutritional habits of the test person.

Figure 2:
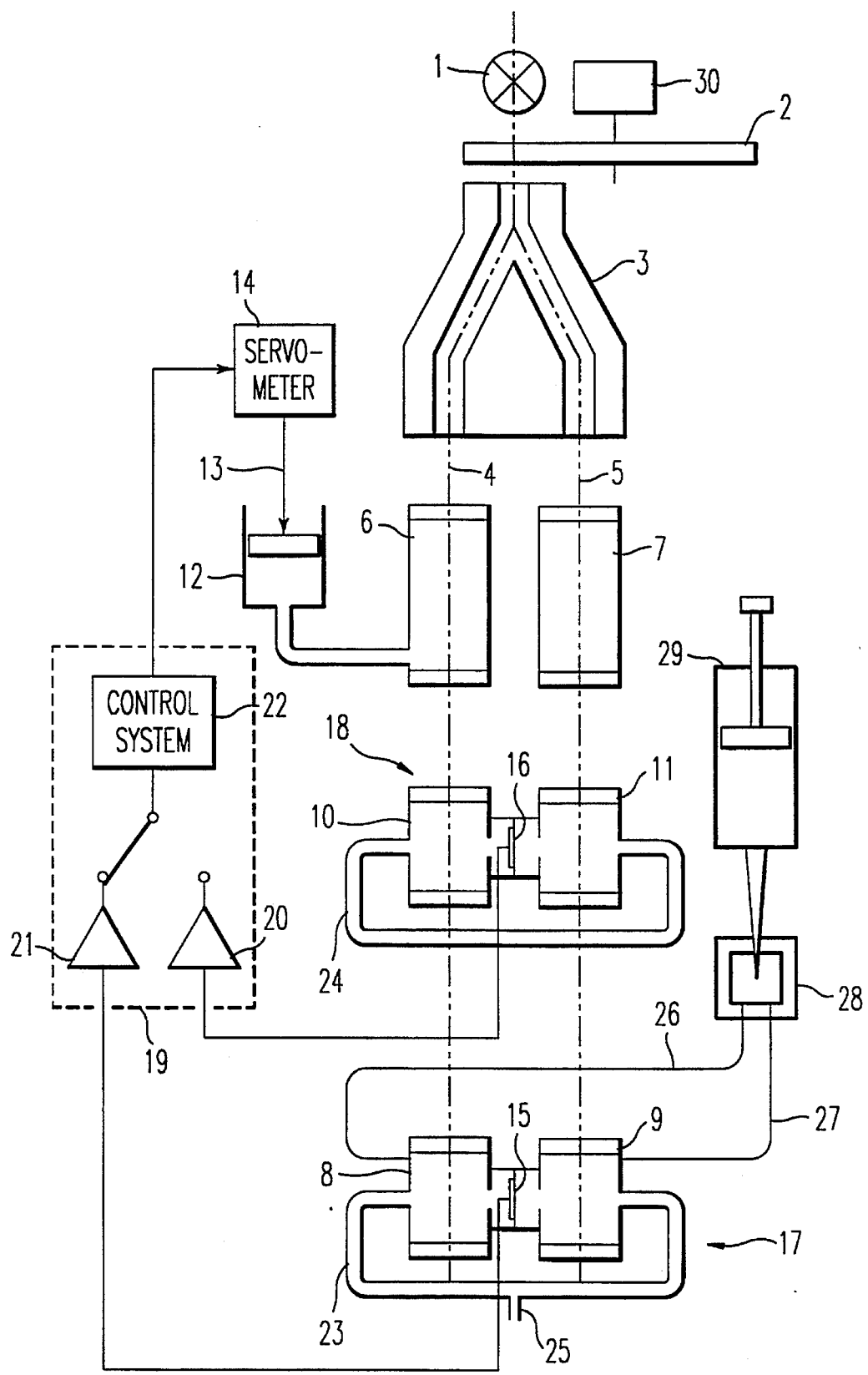
FIG. 2 shows a further embodiment of an apparatus according to the invention with two optopneumatic receivers in which one is filled with a reference gas sample having a known composition.

FIG. 2 shows an embodiment with two optopneumatic receivers 17 and 18. The additionally provided receiver 18, which fundamentally has the same construction as the receiver 17, comprises the cells 10 and 11, the capacitor microphone 16 and the connecting line 24. The cells 10, 11 are placed between the cells 6, 7 on the one hand and the cells 8, 9 of the receiver 17 on the other in the two parallel optical paths 4, 5 and are preferably installed in a fixed manner there. The receiver 18 is used exclusively for determining the reference value. For this purpose the two cells 10 and 11 are permanently filled with a fixed reference gas sample of known composition. Thus, in the case of the receiver 18 there is no need for the individual filling thereof with a reference gas sample. The capacitor microphone 16 is connected to the input of an amplifier 20 in the electronic unit 19. The outputs of the amplifiers 20 and 21 can be alternately connected to the input of the control system 22. Prior to performing the balancing for determining the reference value with the receiver 18, the cells of the receiver 17 are advantageously filled with the gas sample to be analyzed. The reference and measured values can then be determined in directly succeeding manner, which has an advantageous effect on the measuring accuracy by eliminating influences, such as temperature fluctuations, which are not automatically compensated by the balancing process. The second receiver 18 filled with a reference gas obviates manipulations with the reference gas sample, which prevents confusion and makes apparatus operation easier.

Figure 3:
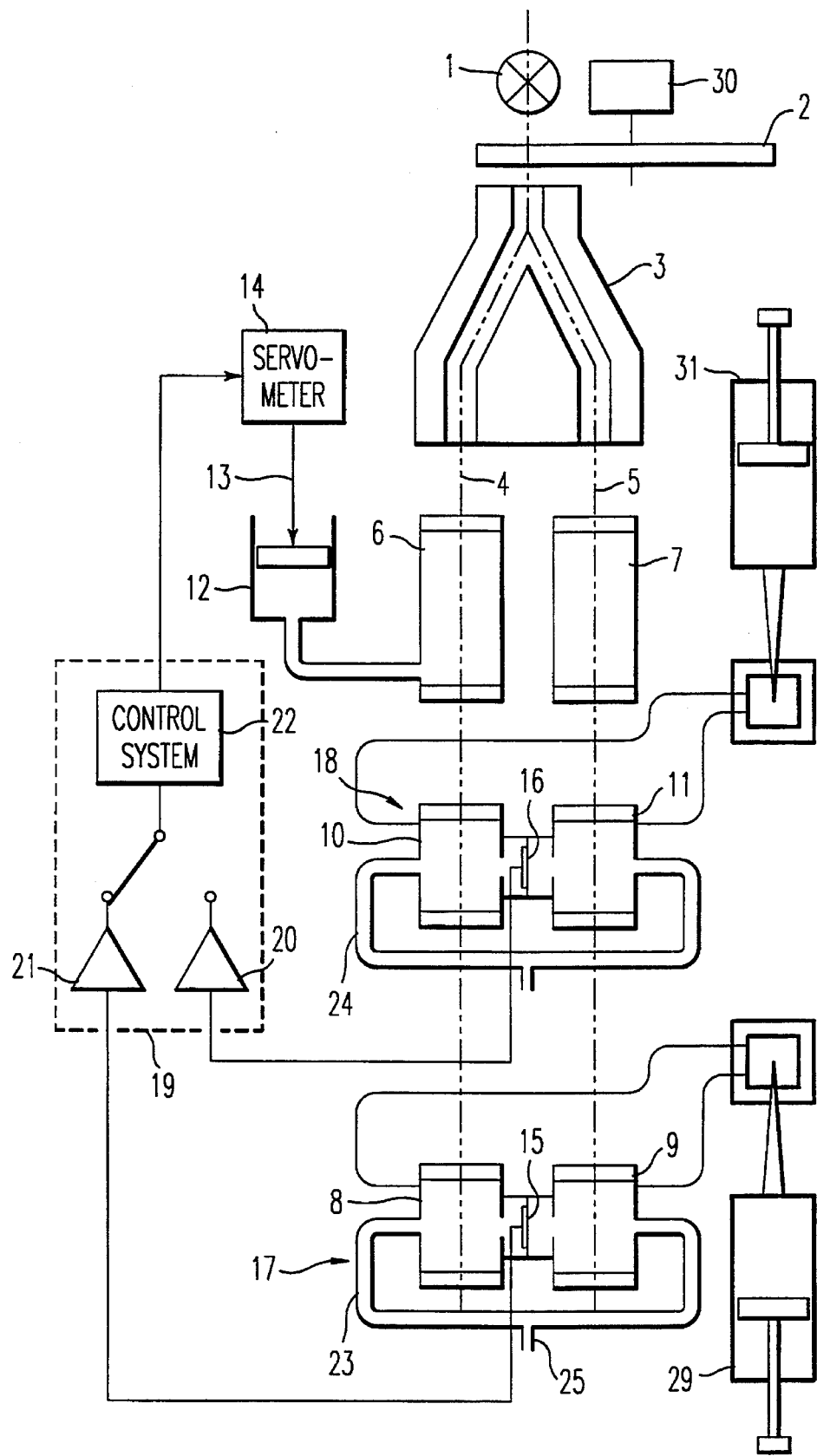
FIG. 3 shows an apparatus according to the invention as in FIG. 2, but in which both optopneumatic receivers can be individually filled with a gas sample.

If it is not wished to accept the measuring errors possibly resulting from the use of a fixed reference gas sample, but still wish to carry out the reference value determination and the actual measurement in directly succeeding manner, the embodiment according to FIG. 3 is appropriate. Once again there are two optopneumatic receivers 17, 18, but the cells 10, 11 of the receiver 18 can be individually filled by means of capillary connections from the syringe 31.

Figure 4:
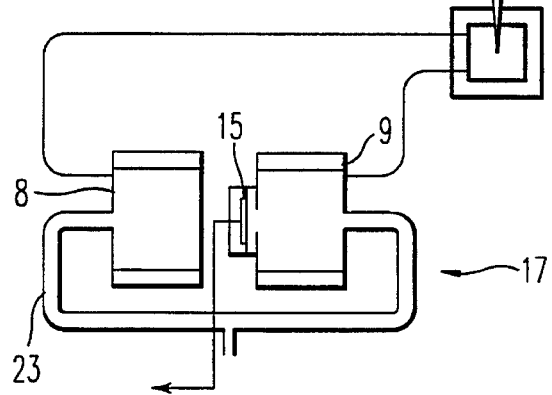
FIG. 4 shows an optopneumatic receiver in which only one of the two cells is associated with the capacitor microphone.

FIG. 4 shows an alternative, technically simpler embodiment of the optopneumatic receivers 17 or 18 by means of the receiver 17. In this case the capacitor microphone 15 is only associated with cell 9. However, it also records the periodic pressure fluctuations in cell 8, because they are also transmitted to it by means of the connecting line 23. They arrive there with a certain time lag, i.e. in phase shifted manner. By an appropriate choice of the length of the connecting line 23 the phase shift can be set to a half-cycle length. On the diaphragm of the capacitor microphone 15 similar conditions then occur as when it is supplied with the differential pressure of both cells 8 and 9.

It is obvious that further elements of the above-described apparatuses can be constructed differently. For instance with respect to producing the two pulsating light beams in the two optical paths, the means for filling cells 8, 9 or 10, 11 and the means used for modifying and adjusting the pressure in the first cell 6. A manual balancing procedure is also possible. The pressure of cell 7 could be regulated in place of that of cell 6. Advantageously a LCD could be used for displaying the set pressure value or the quantity associated therewith. A prior conversion to the ultimately interesting concentration values would be preferable.

In the construction of the apparatus according to the invention with two optopneumatic receivers according to FIGS. 2 or 3, the receiver positioned completely to the rear in the optical path could be filled or charged with the reference gas sample and conversely the receiver 18 positioned in front of it in the optical path can be filled with the gas sample to be analyzed. That such an interchange does not lead to fundamental modifications to the conditions is apparent from the fact that in the case of the reference gas sample it can also be a respiratory gas sample of the patient. The reference gas sample and the gas sample to be analyzed only differ in such a case by the fact that the former was obtained from the patient before ingesting the urea product and the latter subsequently.

The determination of the $^{13}CO_2/^{12}CO_2$ concentration ratio in one of the previously described ways presupposes that the $CO_2$ concentration is known per se and substantially constant, due to the finite thickness of the optopneumatic receiver. As the aim is generally to use alveolar air saturated with $CO_2$ from a single breath of the patient for the measurement (which is readily possible in the case of sample quantities of about 10 ml), this condition is well fulfilled, because saturated alveolar air, inter alia due to the buffering characteristics of the blood has a $CO_2$ concentration in the narrow range 5 to 5.6%. However, if freedom is desired from said restricting condition and/or the measuring errors resulting from possible $CO_2$ concentration fluctuations are to be avoided, separate determination is necessary. This can take place in separate ways with any suitable known measuring method or also directly with the apparatus according to the invention. For this purpose it is merely necessary to carry out a further measurement, in which in the front optopneumatic receiver is provided e.g. a gas (preferably air) substantially not absorbing the infrared light used and balancing is performed with the rear receiver, in which is e.g. located the reference gas sample. The position of the micrometer screw determined during this measurements serves as the zero position $x_0$ of the measuring device relative to which the positions $x_1$ and $x_2$ of the micrometer screw are determined during balancing on the front and rear receivers, when the front receiver is filled with the gas sample to be analyzed. The sought concentration ratio is then obtained as a function of $\Delta x_1 = x_1 - x_0$ and $\Delta x_1 = x_2 - x_0$.

Up to now nothing has been said on the volumes of the optopneumatic receivers and the pulse frequency f of the infrared light (chopper frequency). In fact certain dependencies occur between these quantities and also other parameters and they will now be explained.

With regard to the volumes, they are limited at the high end by the available sample quantities. Generally they should be as small as possible. If for a breathing test e.g. saturated alveolar air from a single breath of the patient is to be sufficient, then the gas sample volume must not significantly exceed 10 ml. The volume of the optopneumatic receiver must then be smaller than 6 ml, preferably smaller than 3 ml.

The amplitude of the pressure fluctuations occurring in the optopneumatic receivers behaves in an approximately inversely proportional manner to the pulse frequency f of the infrared light. Therefore lower frequencies in the range 1 to 150 Hz are preferred compared with higher frequencies. To obtain an adequate signal to noise ratio particularly with respect to impact noise, frequencies above 200 Hz are advantageous (up to approximately 2000 Hz). The amplitude loss due to the 1/f dependence can be compensated by resonance sharpness, if the optopneumatic receivers, as described, are constructed and operated as acoustic resonators. The use of a resonance sharpness of the pressure fluctuations is also appropriate for frequencies above 200 Hz, because there would be an excessive value for the volume of the optopneumatic receivers with frequencies below 200 Hz.

The choice of a frequency above 200 Hz in conjunction with the construction of the optopneumatic receivers as resonant systems has the further advantage that their venting to the environment can take place in simple manner by means of a relatively large hole, if it is ensured that there is a pressure node of the standing wave formed at the location of the hole. In the case of a non-resonant system with a low frequency, venting would have to take place by means of a valve or at least a further capillary.

On the basis of experience up to now a measuring accuracy of better than 10 ppm $^{13}CO_2$ can be obtained with the apparatus according to the invention. A respiratory gas quantity of 10 ml is adequate for performing a measurement.

Obviously, numerous modification and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. Apparatus for the determination of the $^{12}CO_2/^{13}CO_2$-ratio in a gas sample, comprising: an infrared light source and means to pulse said source at a frequency, two first cells traversed in parallel by the light from said light source one containing substantially only $^{13}CO_2$ and the other containing substantially only $^{12}CO_2$; two second cells also traversed in parallel by the light of the infrared light source and in each case containing one part of the gas sample; first pressure converting means having a diaphragm for converting periodic pressure fluctuations caused by the absorption of said light in two of said cells into electrical signals; wherein said two first cells are located in the optical path upstream of said two second cells, the pressure in one of said two first cells is adjustable and the diaphragm of said first pressure converting means is positioned in such a way that it is sensitive to pressure fluctuations in each of said two second cells.

2. Apparatus according to claim 1, wherein the diaphragm of the first pressure converting means constitutes a common wall part of the two second cells and is supplied with differential pressure in the two second cells.

3. Apparatus according to claim 1, wherein the diaphragm of the first pressure converting means is a wall part of only one of the two second cells and is supplied with pressure fluctuations in the other second cell by means of a connecting line between the two second cells.

4. Apparatus according to claim 1, wherein the two second cells communicate with one another by means of a connecting line and the length of said connecting line and the frequency of the means to pulse the infrared light source are chosen in such a way that with respect to the periodic pressure fluctuation in said two second cells there is an antinode of longitudinal wave at the diaphragm of the first pressure converting means.

5. Apparatus according to claim 4, wherein the two second cells are supplied with the gas sample by means of, in each case, one capillary and wherein said connecting line is open to the environment at the point where a node of longitudinal wave occurs during the periodic pressure fluctuations.

6. Apparatus according to claim 1, wherein the pressure in one of the two first cells is adjustable by means of an adjusting screw acting on a diaphragm of a bellows or a pressure cylinder piston.

7. Apparatus according to claim 1, wherein the infrared light source is a low voltage tungsten halogen lamp and the means to pulse is a motor-driven, rotating impeller or a corresponding perforated disk.

8. Apparatus according to claim 1, wherein the light of the infrared light source is split by means of a beam splitter into two equiphase partial beams.

9. The apparatus of claim 8, wherein said partial beams are equal in intensity.

10. Apparatus according to claim 1, wherein a pair of third cells traversed in parallel by the light of the infrared light source and, in each case, containing a part of a reference gas sample are provided, and a diaphragm of a second pressure converting means is positioned in such a way that it is sensitive to pressure fluctuations in each of said two third cells.

11. Apparatus according to claim 10, wherein the diaphragm of the second pressure converting means is a common wall part of the two third cells and is supplied with differential pressure in the two third cells.

12. Apparatus according to claim 10, wherein the diaphragm of the second pressure converting means is a wall part of only one of said two third cells, and pressure fluctuations in the other third cell are transferred to it by means of a connecting line between the two third cells.

13. Apparatus according to claim to 10, wherein the two third cells communicate with one another by means of a connecting line and the length of said connecting line and the frequency of the means to pulse the infrared light source are chosen in such a way that, with respect to the periodic pressure fluctuation in the two third cells, an antinode of longitudinal wave occurs at the diaphragm of the second pressure converting means.

14. Apparatus according to claim 13, wherein the two third cells are supplied by, in each case, one capillary with a reference gas sample and the connecting line is open to the environment at the point where a node of longitudinal wave occurs during the periodic pressure fluctuations.

15. Apparatus according to claim 10, wherein the two third cells are constantly filled with a reference gas sample of known composition.

16. Apparatus according to claim 10, wherein the third cells are located in the optical path between the first and the second cells and are installed there in a fixed manner.

17. Apparatus according to claim 10, wherein the third cells are located in the optical path between the first and the second cells.

18. Apparatus according to claim 10, wherein the volume of the second or third cells, including a connecting line optionally connecting said second cells or said third cells, is smaller than 3 ml.

19. Apparatus according to claim 1, wherein the frequency with which the infrared light source is pulsed is chosen in the range 200 to 2000 Hz.

20. Apparatus according to claim 1, wherein an electrical control and evaluating unit is provided, which, accompanied by a modification of the adjustable pressure in one of said two first cells, determines the amplitude minimum of the electrical signals produced by said first and/or a second pressure converting means and indicates the corresponding pressure value or a quantity corresponding thereto.

* * * * *